United States Patent [19]

Steplewski et al.

[11] Patent Number: 4,971,792
[45] Date of Patent: Nov. 20, 1990

[54] MONOCLONAL ANTIBODIES AGAINST GLYCOLIPID ANTIGENS

[75] Inventors: Zenon Steplewski, Malvern; Hilary Koprowski, Wynnewood; Magdelena Thurin, Philadelphia, all of Pa.

[73] Assignee: The Wistar Institute, Philadelphia, Pa.

[21] Appl. No.: 30,537

[22] Filed: Mar. 27, 1987

[51] Int. Cl.$^5$ .................. A61K 39/395; C07K 15/28
[52] U.S. Cl. .................. 424/85.91; 530/380; 530/381; 530/387; 530/388; 530/389; 530/391; 530/395; 530/806; 530/808; 530/828; 424/93; 435/240.2; 435/240.26; 435/240.27
[58] Field of Search .................. 429/85, 86, 87, 85.8, 429/85.91, 93; 530/387, 809, 828, 808; 435/240.26, 240.27; 935/103

[56] References Cited

U.S. PATENT DOCUMENTS

| | | |
|---|---|---|
| 4,522,918 | 6/1985 | Schlom et al. |
| 4,612,282 | 9/1986 | Schlom et al. |
| 4,675,287 | 6/1987 | Reisfeld et al. .................. 424/85 |
| 4,714,613 | 12/1987 | Shouval et al. .................. 424/85 |
| 4,731,244 | 3/1988 | Talle et al. .................. 424/85 |
| 4,737,579 | 4/1988 | Hellström et al. .................. 424/85 |
| 4,739,279 | 4/1988 | Stephan et al. .................. 424/85 |

OTHER PUBLICATIONS

Blaszczyk-Thurin et al., J. Biol. Chem., 262(1), 372–9, (1987).
Fukushi et al., J. Biol. Chem., 259(7), 4681–5(1984).
Clausen et al., Biochem, 24, 6190–4, (1985).
Gottlinger et al., Int. J. Canc., 38, 47–53, (1986).
Hirohashi et al., PNAS(USA), 82, 7039–43, (1985).
Kimmel et al., JNCI, 75(1), 9–17, (1986).
Hollinshead et al., Cancer, 56, 480–9, (1985).
"Monoclonal Antibodies Specific Immunotherapy of Gastrointestinal Tumors", Douillard, Lehur, Vignoud, Blottiere, Maurel, Thedrez, Kremer and Mevel, Hybridoma vol. 5, Suppl. 1, 1986.
"Effector Cells in ADCC with Anti-Breast Cancer Monoclonal Antibodies in: Monoclonal Antibodies and Breast Cancer", Steplewski, Blaszczyk, Herlyn, Herlyn & Koprowski ed. Ceriani, Published by Nijhoff Publishers, N.Y., N.Y., 1985.
"Differential Expression of Difucosyl Type 2 Chain (Le$^y$) Defined by Monoclonal Antibody AH6 in different Locations of Colonic Epithelia, Various Histological Types of Colonic Polyps, and Adenocarinomas", Abe, Hakomori & Ohshiba Cancer Research, 46, 2639–2644, May, 1986.
"Quantitative and Qualitative Characterization of Human Cancer-Associated Serum Glycoprotein Antigens Expressing Fucosyl or Sailyl-Fucosyl type 2 Chain", Kannagi, Fukushi, Tachikawa, Noda, Shin, Sigeta, Hiraiwa, Fukuda, Inamoto, Hakomori, Imura., Cancer Research 46, 2619–2626, 1986.
"A Spectrum of Monoclonal Antibodies Reactive With Human Mammary Tumor Cells", Colcher, Hand, Nuti & Schlom, Proc. Natl. Acad. Sci. U.S.A. vol. 78, No. 5 pp. 3199–3203, May 1981 Medical Sciences.
"Monoclonal Antobody (B72.3) Defines Patterns of Distribution of A Novel Tumor-Associated Antigen In Human Mammary Carcinoma Cell Populations", Muti, Teramoto, Mariani-Costantini, Hand Colcher & Schlom, J. Cancer: 29, 539–545 (1982).
"Definition of Antigenic Heterogeneity and Modulation Among Human Mammary Carcinoma Cell Populations Using Monoclonal Antibodies to Tumor-Associated Antigens", Hand, Nuti, Colcher & Schlom Cancer Research 43, 728–735, Feb. 1983.

Primary Examiner—Margaret Moskowitz
Assistant Examiner—Jeff Kushan
Attorney, Agent, or Firm—Banner, Birch, McKie & Beckett

[57] ABSTRACT

The present invention is directed to in vitro and in vivo immunodiagnosis and immunotherapy using monoclonal antibodies reactive with difucosyl blood group antigens Y-6 and B-7-2.

12 Claims, No Drawings

MONOCLONAL ANTIBODIES AGAINST GLYCOLIPID ANTIGENS

This work was supported by a Grant from the National Institute of Health. The U.S. Government has certain rights in this invention.

BACKGROUND OF THE INVENTION

1. Field of the Invention

This invention is directed to monoclonal antibodies against human glycolipid antigens, hybrid cell lines producing these monoclonal antibodies, and methods of using these monoclonal antibodies.

2. Description of the Background Art

Adenocarcinomas are carcinomas derived from glandular tissue or in which the tumor cells form recognizable glandular structures. There is increasing evidence suggesting that human adenocarcinomas characteristically express fucolipids representing blood group antigens and chemically related structures (Hakomori, *Annual Reviews of Immunology*, 2: 103-126, 1984). The blood group Y difucosylated hapten is structurally well defined and was first described in ovarian cyst glycoproteins (Lloyd, et al., *Proceedings of the National Academy of Sciences, USA*, 61: 1470-1477, 1968). Later, in its glycolipid form, this hapten was found to be present also in dog intestine (Smith, et al. *Biochimica Biophysica Acta*, 338: 171-179, 1975) and in human fetal intestine (Karlsson, et al., *Journal of Biological Chemistry*, 256: 3512-3524, 1981). More recently, a series of more comples glycolipids with dimeric and trimeric Y determinant structures have been characterized that are more abundant in human erythrocytes of blood group O than of blood group A individuals (Kannagi, et al., *Journal of Biological Chemistry*, 260: 6410-6415, 1985). This determinant has also been found to be present in human liver adenocarcinoma and as an oligosaccharide in the urine of lactating women.

Numerous monclonal antibodies with anti-Y specific activity have been produced by immunizing mice with human gastric cancer, colon cancer, lung cancer, ovarian carcinoma, and human ovarian teratocarcinoma cells. The accumulation of antigens having the Y determinant has been reported in several human adenocarcinomas using the immunoperoxidase technique. The recently reported association between the Y determinant and the carcinoembrionic antigen enhances the relevancy of Y as a diagnostic marker in epithelial adenocarcinomas (Nichols, et al., *Journal of Immunology*, 135: 1911-1913, 1985).

Although the presence of the Y determinant has been found in glycolipid associated with adenocarcinomas, it is unlikely that a monoclonal antibody which reacts solely with an epitope on the Y determinant would be clinically useful. This is because even though in a given tumor mass many of the malignant cells may express an antigen containing the Y determinant it is highly probable that a small, but significant, population of malignant cells will not express the Y determinant and, hence, would probably be refractory to immunotherapy centered on the administration of a Y-specific monoclonal antibody. It is these surviving cells which can enable a recurrence of the tumor mass. Thus, a need exists for a monoclonal antibody which is capable of reacting with an epitope present on multiple determinants of various antigens since such a monoclonal antibody would have far greater clinical efficacy by virtue of its ability to bind to many different populations of adenocarcinoma cells.

SUMMARY OF THE INVENTION

It is a major object of the present invention to provide a method of detecting determinants Y-6 and B-7-2 using a detectably labeled monoclonal antibody which binds to both determinants, and determining whether the detectably labeled monoclonal antibody has bound to these determinants.

Another object of the present invention is to provide methods for the in vitro and in vivo diagnosis of malignancies using detectably labeled monoclonal antibodies which react with an epitope present on determinants Y-6 and B-7-2.

It another object of the invention to provide methods for ameliorating malignant disease in an animal using unlabeled or therapeutically labeled monoclonal antibodies which react with determinants Y-6 and B-7-2.

The present invention thus relates to a method of detecting difucosyl blood group antigens Y-6 and B-7-2 which comprises contacting a source suspected of containing these determinants with a diagnostically effective amount of detectably labeled monoclonal antibody, or fragment thereof, having the specificity of monoclonal antibody BR55-2 and determining whether the antibody binds to the source.

The invention further relates to a method of suppressing malignant disease in an animal which comprises administering to the animal a therapeutically effective amount of a monoclonal antibody, or fragment thereof, wherein said antibody has the specificity of monoclonal antibody BR55-2.

It is a major advantage of the monoclonal antibodies used in the method of the invention that these monoclonal antibodies are capable, unlike the monoclonal antibodies of the prior art, of binding to an epitope which is present on multiple determinants. In so doing, the diagnostic and therapeutic methods of the invention which utilize these monoclonal antibodies are capable of binding to malignant cells which are expressing one or more of these determinants. In addition, since these determinants occur at a much greater frequency on malignant cells than they do on normal tissue there is a much greater probability of binding occurring to a malignant cell than to a normal cell. As a result of this fact, it is possible to use concentrations of the monoclonal antibody of the invention which are clinically effective, but pose minimal or no risk to host cell tissue.

DETAILED DESCRIPTION

The present invention relates to monoclonal antibodies with specificity for antigens indicative of adenocarcinomas as well as other tumors. These monoclonal antibodies are highly useful for both the in vitro and in vivo immunological detection of antigens associated with these tumors and for the immunotherapy of tumors bearing these antigens.

The general method used for production of hybridomas secreting monoclonal antibodies is well known to those of ordinary skill in the art. Illustrative of the techniques utilized in the present invention are those described in *Proceedings of the National Academy of Science, U.S.A.*, 75: 3405, (1978) and Koprowski, U.S. Pat. No. 4,172,124 entitled "Method Of Producing Tumor Antibodies."

Briefly, BALB/c mice were immunized with cultured breast carcinoma cells (MCF 7) and later boosted with the same cell line. After 4 days, the animals were sacrificed and the spleen cells fused with the 653 variant of mouse myeloma P3X63 Ag8. Hybridomas were screened for antibody production and positive clones were tested for reactivity towards cell line MCF 7 and other cancer cell lines. In addition, class-switch variants were produced and isolated using known techniques (Steplewski, et al., *Proceedings of the National Academy Of Science, U.S.A.*, 82: 8653, 1985).

The isolation of other hybridomas secreting monoclonal antibodies with the specificity of the monoclonal antibodies of the invention can be accomplished by one of ordinary skill in the art by the technique of anti-idiotypic screening (Potocnjak, et al., *Science*, 215: 1637, 1982). An anti-idiotypic antibody is an antibody which recognizes unique determinants present on the monoclonal antibody produced by the hybridoma of interest. These determinants are located in hypervariable region of the antibody. It is this region which binds to a given epitope and, thus, is responsible for the specificity of the antibody. The anti-idiotypic antibody can be prepared by immunizing an animal with the monoclonal antibody of interest. The animal immunized will recognize and respond to the idiotypic determinants of the immunizing antibody by producing an antibody to these idiotypic determinants. By using the anti-idiotypic antibodies of the second animal, which are specific for the monoclonal antibodies produced by a single hybridoma which was used to immunize the second animal, it is now possible to identify other clones with exactly the same idiotype as the antibody of the hybridoma used for immunization.

Idiotypic identity between monoclonal antibodies of two hybridomas demonstrates that the two monoclonal antibodies are the same with respect to their recognition of the same epitopic determinant. Thus, by using antibodies to the epitopic determinants on a monoclonal antibody it is possible to identify other hybridomas expressing monoclonal antibodies of the same epitopic specificity.

The present invention is directed to monoclonal antibodies, and hybridomas which produce them, which are reactive with carbohydrate determinants associated with glycolipid and glycoprotein molecules. It can easily be determined whether a monoclonal antibody has the requisite specificity by performing an antigen binding immunoassay such as that described in Thurin, et al. (*Journal of Biological Chemistry*, 262; 372, 1987).

Alternatively, since the inventors have characterized an epitopic moiety to which monoclonal antibodies having the specificity of those of the invention react (Thurin, et al, ibid), it is now a matter of routine skill to produce more hybridomas secreting monoclonal antibodies of identical epitopic specificity. The carbohydrate portion of the Y-6 or B-7-2 blood group determinants, which contain the epitope which binds the monoclonal antibodies of the invention, can be purified from the major portion of the glycolipid by such techniques as ozonolysis (Sabesan, et al., *Canadian Journal Of Chemistry*, 62: 1034, 1984) or by specific enzymatic hydrolysis as with endoglyceroceramidase (Hito, et al., *Journal Of Biological Chemistry*, 262: 14278, 1986). Thus, additional hybridomas secreting monoclonal antibodies having the specificity of monoclonal antibodies produced by cell line ATCC HB 9324 or ATCC HB 9347 can be produced, for example, by coupling this epitope to an inert or immunogenic carrier molecule, such as KLH, to present the epitope in immunogenic form. (Hudson & Hay, *Practical Immunology*, p. 5–8, Blackwell Scientific Publications, 1980). In this manner, animals, can be first immunized with whole Y-6 glycolipid, or cellular fractions enriched in Y-6 glycolipid, for initial sensitization of the animal followed by the conjugated epitope for purified antigen above in the booster immunization to stimulate outgrowth of the preferred B-cell clones.

Alternatively, one could initially immunize with one determinant, such as Y-6, and then boost with a different determinant, such as B-7-2, since the epitope reactive with the monoclonal antibodies of the invention is present on both of these blood group determinants. In any event, since the epitopic specificity of the monoclonal antibodies of the invention has been clearly defined (Thurin, et al., *Journal of Biological Chemistry*, 262; 372, 1987), it is possible to greatly restric the repertoire of responder B-cell clones which are present for hybridoma fusion and thereby avoid undue experimentation in isolating hybridomas of the desired specificity. After fusion, the hybridomas are screened using the epitope and free carrier to select those clones producing monoclonal antibodies which are specific for this epitope.

While the in vivo use of monoclonal antibody from a foreign donor species in a different host recipient species is usually uncomplicated, a potential problem which may arise is the appearance of an adverse immunological response by the host to antigenic determinants present on the donor antibody. In some instances, this adverse response can be so severe as to curtail the in vivo use of the donor antibody in the host. Further, the adverse host response may serve to hinder the malignancy-suppressing efficacy of the donor antibody. One way in which it is possible to circumvent the likelihood of an adverse immune response occurring in the host is by using chimeric antibodies (Sun, et al., *Hybridoma*, 5 (Supplement 1): S17, 1986; Oi et al., *Bio Techniques*, 4 (3): 214, 1986). Chimeric antibodies are antibodies in which the various domains of the antibodies heavy and light chains are coded for by DNA from more than one species. Typically, a chimeric antibody will comprise the variable domains of the heavy ($V_H$) and light ($V_L$) chains derived from the donor species producing the antibody of desired antigenic specificity and the constant antibody domains of the heavy ($C_H$) and light ($C_L$) chains derived from the host recipient species. It is believed that by reducing the exposure of the host immune system to the antigenic determinants of the donor antibody domains, especially those in the $C_H$ region, the possibility of an adverse immunological response occurring in the recipient species will be reduced. Thus, for example, it is possible to produce a chimeric antibody for in vivo clinical use in humans which comprises mouse $V_H$ and $V_L$ domains coded for by DNA isolated from ATCC HB 9324 or ATCC HB 9347 and $C_H$ and $C_L$ domains coded for a DNA isolated from a human cell.

Under certain circumstances, monoclonal antibodies of one isotype might be more preferable than those of another in terms of their diagnostic or therapeutic efficacy. For example, it is known that mouse monoclonal antibodies of isotype gamma-2a and gamma-3 are generally more effective in inhibiting the growth of tumors than is the gamma-1 isotype. This differential efficacy is thought to be due to the ability of the gamma-2a and gamma-3 isotypes to more actively participate in the cytolytic destruction of tumor cells. Particular isotypes of a monoclonal antibody can be prepared either directly, by selecting from the initial fusion, or prepared secondarily, from a parental hybridoma secreting a monoclonal antibody of different isotype by using the sib selection technique to isolate class-switch variants (Steplewski, et al., *Proceedings of the National Academy of Science, U.S.A.*, 82: 8653, 1985; Spira, et al., *Journal of Immunological Methods*, 74: 307, 1984). Thus, the monoclonal antibodies of the invention would include class-switch variants having the speificity of monoclonal antibody BR55-2 which is produced by ATCC HB 9324 or BR55-2-S2a which is produced by ATCC HB 9347.

When the monoclonal antibodies of the invention are used in the form of fragments, such as, for example, Fab and F(ab')$_2$, and especially when these fragments are therapeutically labeled, any isotype can be used since tumor inhibition in these situations is no longer dependent upon complement-mediated cytolytic destruction of the tumor cells.

The monoclonal antibodies of the invention can be used in any animal in which it is desirable to administer in vitro or in vivo immunodiagnosis or immunotherapy. The term "animal" as used herein is meant to include both humans as well as non-humans.

The term "antibody" as used in this invention is meant to include intact molecules as well as fragments thereof, such as, for example, Fab and F(ab')$_2$, which are capable of binding the epitopic determinant.

The monoclonal antibodies of the invention are particularly suited for use in immunoassays in which they can be utilized in liquid phase or bound to a solid phase carrier. In addition, the monoclonal antibodies in these immunoassays can be detectably labeled in various ways. Examples of types of immunoassays which can utilize monoclonal antibodies of the invention are competitive and non-competitive immunoassays in either a direct or indirect format. Examples of such immunoassays are the radioimmunoassay (RIA) and the sandwich (immunometric) assay. Detection of the antigens using the monoclonal antibodies of the invention can be done utilizing immunoassays which are run in either the forward, reverse, or simultaneous modes, including immunohistochemical assays on physiological samples.

The monoclonal antibodies of the invention can be bound to many different carriers and used to detect the presence of adenocarcinoma-associated antigen. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibody, or will be able to ascertain such, using routine experimentation.

There are many different labels and methods of labeling known to those of ordinary skill in the art. Examples of the types of labels which can be used in the present invention include enzymes, radioisotopes, fluorescent compounds, chemiluminescent compounds, and bioluminescent compounds. Those of ordinary skill in the art will know of other suitable labels for binding to the monoclonal antibody, or will be able to ascertain such, using routine experimentation. Furthermore, the binding of these labels to the monoclonal antibody of the invention can be done using standard techniques common to those of ordinary skill in the art.

For purposes of the invention, the adenocarcinoma-associated antigen which is detected by the monoclonal antibodies of the invention may be present in biological fluids and tissues. Any sample containing a detectable amount of adenocarcinoma-associated antigen can be used. Normally, a sample is a liquid such as urine, saliva, cerebrospinal fluid, blood, serum and the like, or a solid or semi-solid such as tissues, feces, and the like.

Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, pyridoxal, and fluoresceine, which can react with specific anti-hapten antibodies.

As used in this invention, the term "epitope" is meant to include any determinant capable of specific interaction with the monoclonal antibodies of the invention. Epitopic determinants usually consist of chemically active surface groupings of molecules such as amino acids or sugar side chains and usually have specific three dimensional structural characteristics, as well as specific charge characteristics.

In using the monoclonal antibodies of the invention for the in vivo detection of antigen, the detectably labeled monoclonal antibody is given in a dose which is diagnostically effective. The term "diagnostically effective" means that the amount of detectably labeled monoclonal antibody is administered in sufficient quantity to enable detection of the site having the difucosyl antigens for which the monoclonal antibodies are specific. The concentration of detectably labeled monoclonal antibody which is administered should be sufficient that the binding to the tumor site is detectable compared to the background signal. Further, it is desirable that the detectably labeled monoclonal antibody be rapidly cleared from the circulatory system in order to give the best tumor-to-background signal ratio.

As a rule, the dosage of detectably labeled monoclonal antibody for diagnosis will vary depending on such factors as age, sex and extent of disease of the individual. The dosage of monoclonal antibody can vary from 0.01 mg/m$^2$ to 20 mg/m$^2$, preferably 0.1 mg/m$^2$ to 10 mg/m$^2$.

For diagnostic in vivo imaging, the type of detection instrument available is a major factor in selecting a given radioisotope. The radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140–250 keV range, which may be readily detected by conventional gamma cameras.

For in vivo diagnosis radioisotopes may be bound to immunoglobin either directly or indirectly by using an intermediate functional group. Intermediate functional groups which often are used to bind radioisotopes which exist as metallic ions to immunoglobins are the bifunctional chelating agents such as, diethylenetriaminepentaacetic acid (DTPA) and ethylenediaminetetraacetic acid (EDTA) and similar molecules.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radiosotopes are used for camera imaging and paramagnetic isotopes for NMR.

The monoclonal antibodies of the invention can be used to monitor the course of malignant disease in an individual. Thus, by measuring the increase or decrease in the size or number of malignant sites, or changes in the concentration of antigen shed into various body fluids, it would be possible to determine whether a particular therapeutic regimen aimed at ameliorating the malignancy is effective.

The monoclonal antibodies of the invention can also be used, alone or in combination with effector cells, for immunotherapy in an animal having a tumor which expresses adenocarcinoma-associated difucosyl blood group antigens with epitopes reactive with the monoclonal antibodies of the invention. When used in this manner, the dosage of monoclonal antibody can vary from 10 mg/m$^2$ to 2000 mg/m$^2$. The term "therapeutically effective" means that the amount of monoclonal antibody used is of sufficient quantity to ameliorate the cause of disease due to the malignancy.

When used for immunotherapy, the monoclonal antibodies of the invention may be unlabeled or labeled with a therapeutic agent. These agents can be coupled either directly or indirectly to the monoclonal antibodies of the invention. One example of indirect coupling is by use of a spacer moiety. These spacer moieties, in turn, can be either insoluble or soluble (Diener, et al., Science, 231: 148, 1986) and can be selected to enable drug release from the monoclonal antibody molecule at the target site. Examples of therapeutic agents which can be coupled to the monoclonal antibodies of the invention for immunotherapy are drugs, radioisotopes, immunomodulators, lectins and toxins.

The drugs with which can be conjugated to the monoclonal antibodies of the invention include non-proteinaceous as well as proteinaceous drugs. The term "non-proteinaceous drugs" encompasses compounds which are classically referred to as drugs such as for example, mitomycin C, daunorubicin, and vinblastine.

The proteinaceous drugs which the monoclonal antibodies of the invention can be labeled include immunomodulators and other biological response modifiers. The term "biological response modifiers" is meant to encompass substances which are involved in modifying the immune response in such manner as to enhance the destruction of the tumor cells bearing the difucosyl blood group antigen for which the monoclonal antibodies of the invention are specific. Examples of immune response modifiers include such compounds as lymphokines. Examples of lymphokines include tumor necrosis factor, interleukins 1, 2, and 3, lymphotoxin, macrophage activating factor, migration inhibition factor, colony stimulating factor and interferon. Interferons with which the monoclonal antibodies of the invention can be labeled include alpha-interferon, beta-interferon, and gamma-interferon and their subtypes.

In using radioisotopically conjugated monoclonal antibodies of the invention for immunotherapy certain isotypes may be more preferable than others depending on such factors as tumor distribution and mass as well as isotype stability and emission. If desired, the tumor distribution and mass can be evaluated by the in vivo diagnostic techniques described supra. Depending on the type of malignancy present some emitters may be preferable to others. In general, alpha and beta particle-emitting radioisotopes are preferred in immunotherapy. For example, if an animal has solid tumor foci a high energy beta emitter capable of penetrating several millimeters of tissue, such as $^{90}$Y, may be preferable. On the other hand if the malignancy consists of single target cells, as in the case of leukemia, a short range, high energy alpha emitter such as $^{212}$Bi may be preferred. Examples of radioisotopes which can be bound to the monoclonal antibodies of the invention for therapeutic purposes are $^{125}$I, $^{131}$I, $^{90}$Y, $^{67}$Cu, $^{212}$Bi, $^{211}$At, $^{212}$Pb, $^{47}$Sc, $^{109}$Pd and $^{188}$Re.

Lectins are proteins, usually isolated from plant material, which bind to specific sugar moieties. Many lectins are also able to agglutinate cells and stimulate lymphocytes. However, ricin is a toxic lectin which has been used immunotherapeutically. This is accomplished by binding the alpha-peptide chain of ricin, which is responsible for toxicity, to the antibody molecule to enable site specific delivery of the toxic effect.

Toxins are poisonous substances produced by plants, animals, or microorganisms that, in sufficient dose, are often lethal. Diphtheria toxin is a substance produced by Corynebacterium diphtheriae which can be used in this manner. This toxin consists of an alpha and beta subunit which under proper conditions can be separated. The toxic A component can be bound to antibody and used for site specific delivery to a tumor expressing the difucosyl antigens for which the monoclonal antibodies of the invention are specific.

Other therapeutic agents which can be coupled to the monoclonal antibodies of the invention are known, or can be easily ascertained, by those of ordinary skill in the art.

The labelled or unlabelled monoclonal antibodies of the invention can also be used in combination with therapeutic agents such as those described supra. Especially preferred are therapeutic combinations comprising the monoclonal antibody of the invention and immunomodulators and other biological response modifiers.

Thus, for example, the monoclonal antibodies of the invention can be used in combination with alpha-interferon. This treatment modality enhances monoclonal antibody targeting of carcinomas by increasing the expression of monoclonal antibody reactive antigen by the carcinoma cells (Greiner, et al., Science, 235:895, 1987). Alternatively, the monoclonal antibody of the invention could be used, for example, in combination with gamma-interferon to thereby activate and increase the expression of Fc receptors by effector cells which, in turn, results in an enhanced binding of the monoclonal antibody to the effector cell and killing of target tumor cells. Those of skill in the art will be able to select from the various biological response modifiers to create a desired effector function which enhances the efficacy of the monoclonal antibody of the invention.

When the monoclonal antibody of the invention is used in combination with various therapeutic agents, such as those described herein, the administration of the monoclonal antibody and the therapeutic agent usually occurs substantially contemporaneously. The term "substantially contemporaneously" means that the monoclonal antibody and the therapeutic agent are administered reasonably close together with respect to time. Usually, it is preferred to administer the therapeutic agent before the monoclonal antibody. For example, the therapeutic agent can be administered 1 to 6 days before the monoclonal antibody. The administration of the therapeutic agent can be, daily or at any other interval depending upon such factors, for example, as the nature of the tumor, the condition of the patient and half-life of the agent.

Using the monoclonal antibodies of the invention, it is possible to design, therapies combining all of the characteristics described herein. For example, in a given situation it may be desirable to administer a therapeutic agent, or agents, prior to the administration of the monoclonal antibodies of the invention in combination with effector cells and the same, or different, therapeutic agent or agents. For example, it may be desirable to treat patients with adenocarcinoma by first administering gamma-interferon and interleukin-2 daily for 3 to 5 days, and on day 5 administer the monoclonal antibody of the invention in combination with effector cells as well as gamma-interferon, and interleukin-2.

It is also possible to utilize liposomes with the monoclonal antibodies of the invention in their membrane to specifically deliver the liposome to the area of the tumor expressing difucoysl blood group antigens Y-6 or B-7-2. These liposomes can be produced such that they contain, in addition to the monoclonal antibody, such immunotherapeutic agents as those described above which would then be released at the tumor site (Wolff, et al., *Biochemica et Biophysica Acta*, 802: 259, 1984).

The dosage ranges for the administration of the monoclonal antibodies of the invention are those large enough to produce the desired effect in which the symptoms of the difucosyl expressing tumor are ameliorated. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counter indications, immune tolerance or similar conditions. Dosage can vary from 0.1 mg/m$^2$ to 2000 mg/m$^2$, preferably 0.1 mg/m$^2$ to 500 mg/m$^2$/dose, in one or more dose administrations daily, for one or several days. Generally, when the monoclonal antibodies of the invention are administered conjugated with therapeutic agents lower dosages, such as those used for in vivo immunodiagnostic imaging, can be used.

The monoclonal antibodies of the invention can be administered parenterally by injection or by gradual perfusion over time. The monoclonal antibodies of the invention can be administered intravenously, intraperitoneally, intramuscularly, subcutaneously, intracavity, or transdermally, alone or in combination with effector cells.

Preparations for parenteral administration include sterile aqueous or non-aqueous solutions, suspensions, and emulsions. Examples of non-aqueous solvents are propylene glycol, polyethylene glycol, vegetable oils such as, olive oil, and injectable organic esters such as ethyl oleate. Aqueous carriers include water, alcoholic-/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, and inert gases and the like.

The invention also relates to a method for preparing a medicament or pharmaceutical composition comprising the monoclonal antibodies of the invention, the medicament being used for therapy of tumors expressing the difucosyl blood group antigens reactive with the monoclonal antibodies of the invention.

Monoclonal antibody can be utilized in the present invention. BR55-2 is obtained from, or has the identifying characteristics of, an antibody obtained from the cell line having ATCC accession number HB 9324. BR55-2-S2a is obtained from, or has the identifying characteristics of, an antibody obtained from the cell line having ATCC accession number HB 9347. These cell lines were placed on deposit for 30 years at the American Type Culture Collection (ATCC) in Rockville, Md. prior to Mar. 27, 1987.

The above disclosure generally describes the present invention. A more complete understanding can be obtained by reference to the following specific examples which are provided herein for purposes of illustration only, and are not intended to limit the scope of the invention.

EXAMPLE 1

Preparation of Hybridoma Cell Lines Producing Monoclonal Antibodies to Adenocarcinoma-Associated Antigens A. Immunization and Production of Hybridomas BALB/c mice were immunized intraperitoneally with $2 \times 10^7$ cells of breast adenocarcinoma MCF-7 and boosted intravenously four weeks later with $1 \times 10^6$ cells. Four days later, the animals were sacrificed and spleen cells fused with the 653 variant of mouse melanoma P3X63 Ag8. The growth, cloning and maintenance of the hybridomas produced was as described by Koprowski, et al. (*Somatic Cell Genetics*, 5: 957, 1979). Monoclonal antibodies produced by the various hybridomas were screened for antibody production and positive clones were further screened for reactivity towards cell line MCF-7 and no reactivity toward human melanoma cell line WM164 and others. Selected cultures were then cloned using the limiting dilution technique. Hybridoma class-switch variants were produced using the procedures described by Steplewski, et al. (*Proceedings of the National Academy of Sciences, U.S.A.*, 82: 8653, 1985). The characterization of the epitopic specificity of BR 55-2 and BR 55-2-S2a has been described (Thurin, et al., *Journal Of Biological Chemistry*, 262: 372, 1987). Monoclonal antibodies were purified for clinical testing according to Sears, et al. (*THE LANCET*, 762, Apr. 3, 1982).

B. Glycolipids

The purification and characterization of the various blood group antigens was performed essentially using the techniques described in Thurin, et al. (*Journal Of Biological Chemistry*, 260: 14556, 1985).

EXAMPLE 2

In Vivo Clinical Trials in Humans Using BR55-2-S2a

Patients with terminal gastrointestinal cancer which presented with recurrence, metastasis or unresectable tumors were included in the study if they were less than 75 years old, with a Karnosky index greater than 60, with a life expectancy of more than 3 months and when the primary tumor type was clearly identified as a gastrointestinal tract adenocarcinoma using biopsy material.

Patient tumors, or when available, metastasis biopsy specimens, were studied for antigenic expression using monoclonal antibodies BR55-2-S2a, CO 19-9, GA 73-3 and CO 17-1A. Based on these individual immunohistochemical results, a cocktail of monoclonal antibodies was administered to the patient.

In treating the patients, autologous peripheral blood mononuclear cells were obtained by leukophoresis, through a routine procedure using an IBM 2997 blood cell separator to yield a total number of $1 \times 10^9$ to $1 \times 10^{10}$ mononuclear cells. The cells obtained by leukophoresis were collected in a sterile plastic bag with a total volume of 160 to 200 ml. The monoclonal antibodies (150–200 mg of each) for which the patient tumor was reactive were then injected directly into the leukobag and allowed to incubate at room temperature at one hour, with gentle shaking every 15 minutes. In so doing, the monoclonal antibodies were able to bind to effector cells via Fc receptors on the surface of the cells and thereby act as a vector for effector cell targeting to the tumor. Sampling of free monoclonal antibody in the supernatant from the leukobag showed that, on the average, 40% of the amount of injected antibody bound to the autologous cells. After this incubation period, the mixture of autologous cells and free monoclonal antibodies in the leukobag were reinfused into a peripheral vein, or into the hepatic artery, over a period of 2 to 3 hours. After infusion, the line was kept in the blood vessel in order to treat possible delayed side affects. Patients were carefully checked for blood pressure, pulse, chills, skin rash, bronchio-spasm or any other suspect clinical signs during infusion and again 24 hours thereafter. The result of Phase I clinical trials are shown in Table 1.

TABLE 1

RESULTS OF PHASE I CLINICAL TRIALS USING BR55-2-S2a[a]

| CANCER DIAGNOSIS | | | MONTHS STABLE IN RESPONSE TO THERAPY[b] |
|---|---|---|---|
| ORIGIN | METASTASES | PATIENT | |
| colon | liver | 9 | |
| | | 14 | 6 |
| | | 25 | 6,+ |
| | | 39 | 7,+ |
| | lung | 12 | 0 |
| | | 26 | 8,+ |
| | liver,pleura | 34 | 0 |
| | liver,lung | 40 | 7,+ |
| | skin | 36 | 0 |
| | local lymph nodes | 43 | 6 |
| breast | bone,skin | 2 | tumor regression |
| | pleura,skin | 27 | 5,+ |
| rectal | liver | 10 | 2 |
| | | 15 | 2 |
| | | 17 | 5 |
| | | 30 | 15 |
| | | 33 | 8,+ |
| gastric | local recurrence | 18 | 3 |
| | lung | 38 | 7,+ |
| pancreas | unresectable liver | 20 | 9 |
| | | 22 | 8 |
| | | 31 | 2 |
| | liver, lymph nodes | 32 | 6 |

TABLE 1-continued

RESULTS OF PHASE I CLINICAL TRIALS USING BR55-2-S2a[a]

| CANCER DIAGNOSIS | | | MONTHS STABLE IN RESPONSE TO THERAPY[b] |
|---|---|---|---|
| ORIGIN | METASTASES | PATIENT | |
| | lymph nodes | 35 | 1 |

[a]gamma-2A variant in admixture with other monoclonal antibodies and effector cells
[b]"+" denotes that patient was still stable at time of data compilation The cancer patients treated with BR55-2-S2a had primary tumor foci of the colon (10), breast (2), rectum (5), gastric tract (2) and pancreas (5). As noted, all patients had some degree of metastases. This data is further summarized in Table 2.

TABLE 2

CLINICAL SUMMARY

| | | RESPONSE | | |
|---|---|---|---|---|
| TUMOR ORIGIN | NUMBER OF PATIENTS | NONE | TEMPORARY STABILITY | CONTINUING STABILITY |
| colon | 10 | 4 | 2 | 4 |
| breast | 2 | — | — | 4[a] |
| rectal | 5 | — | 4 | 1 |
| gastric | 2 | — | 1 | 1 |
| pancreas | 5 | — | 5 | — |
| total | 24 | 4 | 12 | 8 |

[a]one patient had tumor regression

As shown here, of the 24 patients in this study receiving BR55-2-S2a, 4 apparently did not respond to the monoclonal antibody therapy. Of the 20 patients responding favorably to therapy, 12 were temporarily stable for an average of 5.3 months. The eight remaining patients who responded to therapy were still stable at the time the data was tabulated. Among this group of patients showing continued stability, the average response to therapy was 6.9 months and included 1 patient who had experienced tumor regression.

The invention now being fully described, it will be apparent to one of ordinary skill in the art that many changes and modifications can be made without departing from the spirit or scope of the invention.

We claim:

1. A method of treating malignant disease in an animal having a malignant tumor which expresses an epitope reactive with the monoclonal antibody produced by cell line ATCC HB 9324, which method comprises:
   administering to said animal a therapeutically effective amount of a monoclonal antibody, or fragment thereof, wherein said antibody has the specificity of monoclonal antibody BR55-2 produced by ATCC HB 9324.

2. The method of claim 1, wherein said monoclonal antibody is produced by a cell line selected from the group consisting of ATCC HB 9324 and ATCC HB 9347.

3. The method of claim 1, wherein said malignant disease is adenocarcinoma.

4. The method of claim 1, wherein said administration is parenteral.

5. The method of claim 4, wherein said parenteral administration is by subcutaneous, intramuscular, intraperitoneal, intracavital, or intravenous injection.

6. The method of claim 1, wherein said administration is at a dosage of about 0.01 mg/m$^2$ to about 2000 mg/m$^2$.

7. The method claim 1, wherein said antibody is administered in combination with effector leukocytes.

8. The method of claim 1, wherein said antibody is therapeutically labeled.

9. The method of claim 8, wherein said therapeutic label is selected from the group consisting of a radioisotope, a drug, an immunomodulator, a biological response modifier, a lectin and a toxin.

10. The method in any of claims 1, 7 and 8, wherein said antibody is administered substantially contemporaneously in combination with an immunomodulator.

11. The method of claim 10, wherein said administration of said immunomodulator is from about 1 to about 6 days before the administration of said antibody.

12. The method of claim 7 where the effector cells are autologous peripheral blood mononucleocytes.

* * * * *